United States Patent

Bütefisch

[11] Patent Number: 5,935,459
[45] Date of Patent: Aug. 10, 1999

[54] TEST DEVICE FOR IMPINGING A SAMPLE WITH A HIGH-ENERGY GAS JET

[75] Inventor: Karl-Aloys Bütefisch, Bovenden, Germany

[73] Assignee: Deutsches Zentum fur Luft und Raumfahrt e.V., Germany

[21] Appl. No.: 08/985,925

[22] Filed: Dec. 5, 1997

[30] Foreign Application Priority Data

Dec. 21, 1996 [DE] Germany .................... 196 53 887

[51] Int. Cl.⁶ .................................................. B23K 10/00
[52] U.S. Cl. ........................... 219/121.52; 219/121.48; 219/119; 60/271; 315/111.21
[58] Field of Search .................. 219/121.48, 121.39, 219/121.52, 121.59, 74, 75, 119; 313/231.3–231.4; 60/271; 315/111.21

[56] References Cited

U.S. PATENT DOCUMENTS

| | | |
|---|---|---|
| 3,311,735 | 3/1967 | Winzeler et al. .................. 219/121.52 |
| 4,727,236 | 2/1988 | Hull et al. ......................... 219/121.52 |
| 5,207,388 | 5/1993 | Leroux et al. ...................... 239/598 |

*Primary Examiner*—Mark Paschall
*Attorney, Agent, or Firm*—Womble Carlyle Sandridge & Rice

[57] ABSTRACT

A test device (1) serves for impinging a sample (2) with a high-energy gas jet (3). A plasma torch (4, 5) provides the gas jet (3) heated by a plasma and directed towards the sample (2). A massive metal plate (6) is positioned in front of the sample (2). The metal plate (6) forms the opposing electrode for the plasma torch (4-6). A drive system (7) is provided for rotating the metal plate (6) about an rotational axis (9). The metal plate (6) is provided with a gap (11) exposing the sample (2) to the gas jet (3) when the metal plate (6) is in a certain rotational position about the rotational axis (9).

9 Claims, 2 Drawing Sheets

TEST DEVICE FOR IMPINGING A SAMPLE WITH A HIGH-ENERGY GAS JET

FIELD OF THE INVENTION

The invention is generally related to a test device for impinging a sample with a high-energy gas jet. More particularly the invention is related to a test device for impinging a sample with a high-energy gas jet in order to simulate, for example, aerodynamic loads exerted on materials to be tested, the test device comprising a plasma torch providing the gas jet heated by a plasma and directed towards the sample.

BACKGROUND OF THE INVENTION

The behaviour of materials in the case of impingement with high-energy gas jets is always of importance if materials are selected for applications, in which said gas jets occur or might occur.

This is, for example, the case in materials, which form the surface of a missile's seeker head. These materials must maintain transparency even in case of high Mach numbers. Typically, the relevant material properties are to be maintained for a limited period only, since impingement with high-energy gas jets actually also occurs for a short period only. Thus, it is in principle sufficient to carry out impingement with a high-energy gas jet for a limited period of time when the materials are tested.

A test device according to the type described above is known from U.S. Pat. No. 5,207,388. This older U.S. Patent describes the testing of materials, which are exposed to high thermal and pressure stress, such as in space missiles, by impinging a material sample with a high-energy gas jet. Particularly, the older U.S. Patent refers to the design of a nozzle which forms the output of a plasma torch and which directs the high-energy gas jet onto the sample.

This and other known test devices for impinging a sample with a high-energy gas jet are characterized by a stationary structure. A certain period of time passes during each individual test until the gas jet, hitting the sample, has stabilized and until defined impinging conditions are present. Uncontrolled conditions also occur during switch-off of the gas jet, after the actual test has been completed. Starting and stopping the test device have particularly negative effects if a defined impingement with the gas jet is to be carried out for a very short period only.

Other known test devices for impinging a sample with a high-energy gas jet are based on wind tunnels or test sledges, which are normally used for detecting aerodynamically derived forces. Operation of wind tunnels or test sledges for impinging a sample with a high-energy gas jet is extremely cost-intensive.

OBJECT OF THE INVENTION

It is the object of the invention to provide a test device for impinging a sample with a high-energy gas jet, which can, on one hand, be operated with low expenditure and which, on the other hand, enables impinging a sample with a defined gas jet for defined short periods.

SUMMARY OF THE INVENTION

Briefly, the invention is a test device for impinging a sample with a high-energy gas jet, the test device comprising a plasma torch providing the gas jet heated by a plasma and directed towards the sample, wherein a massive metal plate is positioned in front of the sample, the metal plate forming the opposing electrode of the plasma torch, wherein drive means are provided for rotating the metal plate about an rotational axis, and wherein the metal plate is provided with a gap exposing the sample to the gas jet when the metal plate is in a certain rotational position about the rotational axis.

In the test device according to the invention, the gas jet is provided by a plasma torch. Plasma torches are well-known and are usually used for cutting metal and other materials. Although undefined conditions occur over certain periods when igniting and extinguishing the plasma torch, they are not relevant here, since the gas jet does not hit the sample during these periods but is prevented therefrom by the massive metal plate. Only after the plasma in the plasma torch and, thus, the heated gas jet have stabilized, the metal plate will be rotated about its rotational axis in such a manner that the sample is exposed to the gas jet through the gap. The metal plate is further rotated after and/or during the specified impingement period so that the gas jet subsequently hits the metal plate again. Then, the plasma torch can be extinguished, without causing undefined test conditions.

The metal plate is preferably rotated continuously, so that the gap crosses the heated gas jet, thus releasing it onto the sample.

The metal plate is preferably also rotated when hit by the gas jet in order to avoid the gas jet burning a hole in the metal plate. Local melting of the metal plate on the impact point of the gas jet is acceptable. When the metal plate is rotated further, the molten material again solidifies in this area, since melting heat is conducted to the surrounding material.

The new test device consists of the most simple components and is nevertheless suited to carry out defined short-time impingement of a sample with a high-energy gas jet.

In principle, the metal plate can also have several gaps. But this is normally not necessary. The gap(s) can have a straight or round shape, a round cross section being preferred due to the symmetric arrangement around a gas jet having a round cross section.

In order to be able to exactly specify the metal plate's rotational positions about the rotational axis, a rotary drive, which can be controlled with respect to the rotational position of the metal plate, can be provided. A computer-controlled pulse motor, for example, can be used for this purpose.

When the gas jet hits the metal plate at the bottom of a ring-shaped groove in the surface of the metal plate, molten metal is prevented from running off from the metal plate's surface.

Said groove preferably has a rounded cross section so that the surface tension exhibited by the molten metal is used for keeping the metal in its original place.

The bottom of the groove can be provided with a ceramic cover. This ceramic cover prevents melting of the metal plate on its surface. Then, the metal of the metal plate, bordering the bottom of the groove, serves as the opposing electrode for the plasma torch and for carrying away and distributing the resulting heat from the ceramic cover.

The gap can also be provided with a ceramic lining in order to protect the metal plate from the high-energy gas jet.

A rounded cross section in the groove avoids occurrence of field peaks on the metal plate's surface. The ceramic cover in the position where the gas jet hits the metal plate and the ceramic lining of the gap ensure that the flow of ions has approximately the same course, independent of the fact of whether the gas jet is absorbed by the metal plate or hits the sample through the gap. In both cases, they tend to flow to those regions of the metal plates bordering the sides of the ceramic cover or the ceramic lining, respectively.

The metal plate can not only be provided as an opposing electrode, but also as an ignition electrode for the plasma torch.

To avoid any charging effects during impinging the sample with a high-energy gas jet, an absorption electrode for removing charged particles from the gas jet can be arranged in front of the sample.

Neutrality of the gas jet can be monitored in front of the sample with a Langmuir probe, whereby the number of charged particles can be quantified by means of a current occurring due to the absorption potential.

In the following, the invention is explained and described in detail on the basis of two preferred embodiments.

DETAILED DESCRIPTION OF THE PREFERRED EMBODIMENTS

Figure 1:
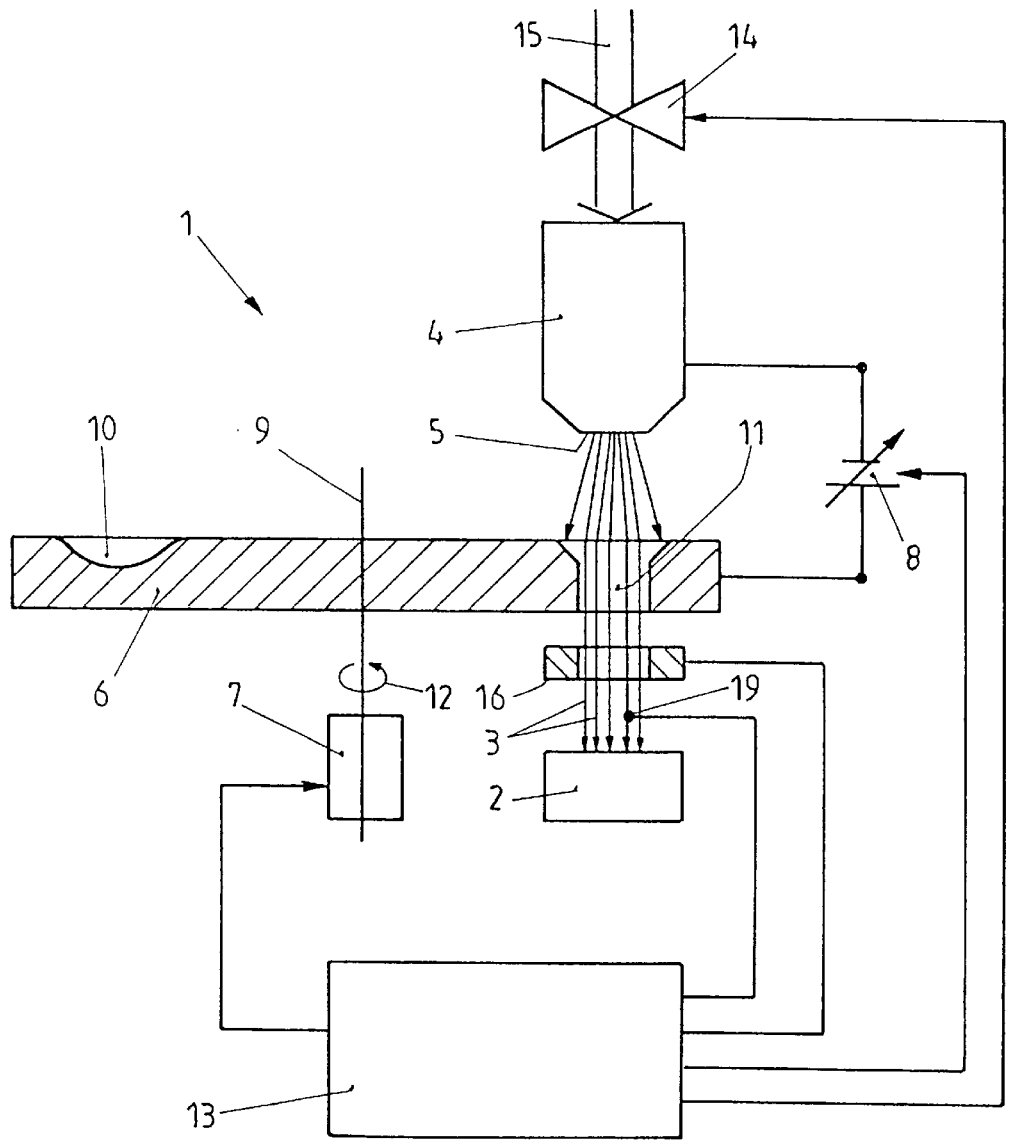
FIG. 1 shows the principle structure of a first embodiment of the test device.

A test device 1 shown in FIG. 1 serves for defined impingement of a sample 2 with a high-energy gas jet 3, which is shown here in form of dashed lines. The gas jet 3 originally emerges from a component 4, which is provided with an ignition electrode 5 and which is here always termed the plasma torch 4, although the full plasma torch also comprises an opposing electrode, which is formed by metal plate 6, here outside of the component 4. A high voltage 8 is applied between the plasma torch 4 and the metal plate 6, maintaining a light-arc discharge between the plasma torch 4 and the metal plate 6, which light-arc discharge has initially been generated by means of the ignition electrode 5. This means that the plasma heating the gas jet 3 burns between the plasma torch 4 and the metal plate 6. In the rotational position of the metal plate 6 about the rotational axis 9 as presented in FIG. 1, the gas jet 3 then reaches the sample 2. Otherwise, the gas jet 3 hits the metal plate 6 at the bottom of a groove 10 having a rounded cross section, thus being restrained. Local melting of the metal plate 6 occurs. But the molten metal is kept in its original place by the surface tension supported by the shape of the groove 10. Rotation of the metal plate 6 about the rotational axis 9 prevents the gas jet 3 from burning a hole in the metal plate 6. The gap 11, through which the gas jet 3 hits the sample 2 in the rotational position of the metal plate 6 about the rotational axis 9 as shown in FIG. 1, has been intentionally integrated in the metal plate 6 and serves as an aperture for the gas jet 3. The metal plate 6 is rotated, in the direction of an rotary arrow 12, by a rotary drive 7, which can be controlled by controlling device 13 with respect to the position of the metal plate 6 rotating about the rotational axis 9. It is not only important to rotate the metal plate 6 for arranging the gap 11 for a defined period of time above the sample 2 so that the gas jet 3 impinges on sample 2. Continuous rotation of the metal plate 6 is also useful to allow for the impinging gas jet to melt the metal plate 6 locally without affecting it for such a long time that a hole is burnt in the metal plate 6. The controlling device 13 further controls the gas flow through the plasma torch 4 by means of a valve 14, which is positioned in a gas feeding line 15 of plasma torch 4. The controlling device 13 is also provided for regulating the high voltage 8 between the plasma torch 4 and the metal plate 6. For example, high voltage 8 can be distinctly decreased after igniting the plasma for maintaining the plasma only. In addition, the controlling device 13 applies an absorption potential to an absorption electrode 16 between the metal plate 6 and the sample 2 in order to remove charged particles from the gas jet 3. Thus, charging effects during impinging the sample 2 with the gas jet 3 are prevented. The absorption electrode 16 can be provided either for absorbing electrons or gas ions. This depends on the potential applied. By means of a Langnuir probe, the controlling device 13 determines which type of charged particles are present in excess in the gas jet 3 and should be absorbed. In addition to the absorption electrode 16, a second absorption electrode can also be provided so that both negative and positive particles can be removed from the gas jet 3.

In operating the test device 1 according to FIG. 1, it is particularly intended to ignite the plasma between the plasma torch 4 and the metal plate 6 by means of the ignition electrode 5 and extinguishing the plasma, when the sample 2 is covered by the metal plate 6. Only after the plasma has stabilized, the gap 11 will be rotated for a defined period of time above the sample 2. All the other time, the metal plate 6 is rotated under the plasma torch 4 in order to cover sample 2, without burning through the metal plate 6.

Figure 2:
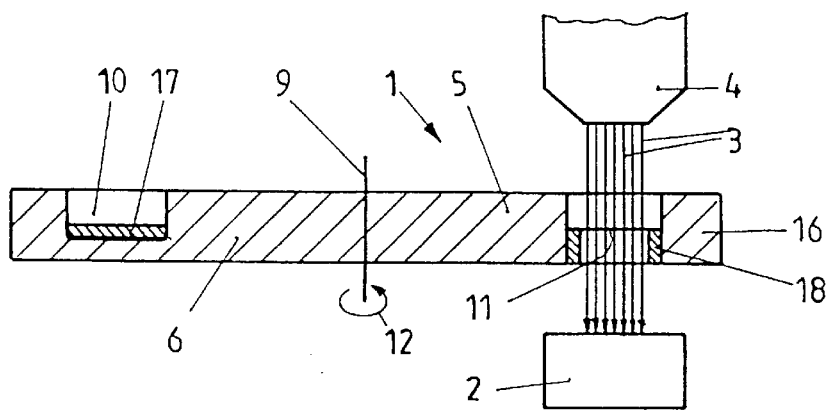
FIG. 2 shows a second embodiment of the test device with the details deviating from the embodiment shown in FIG. 1
Figure 3:
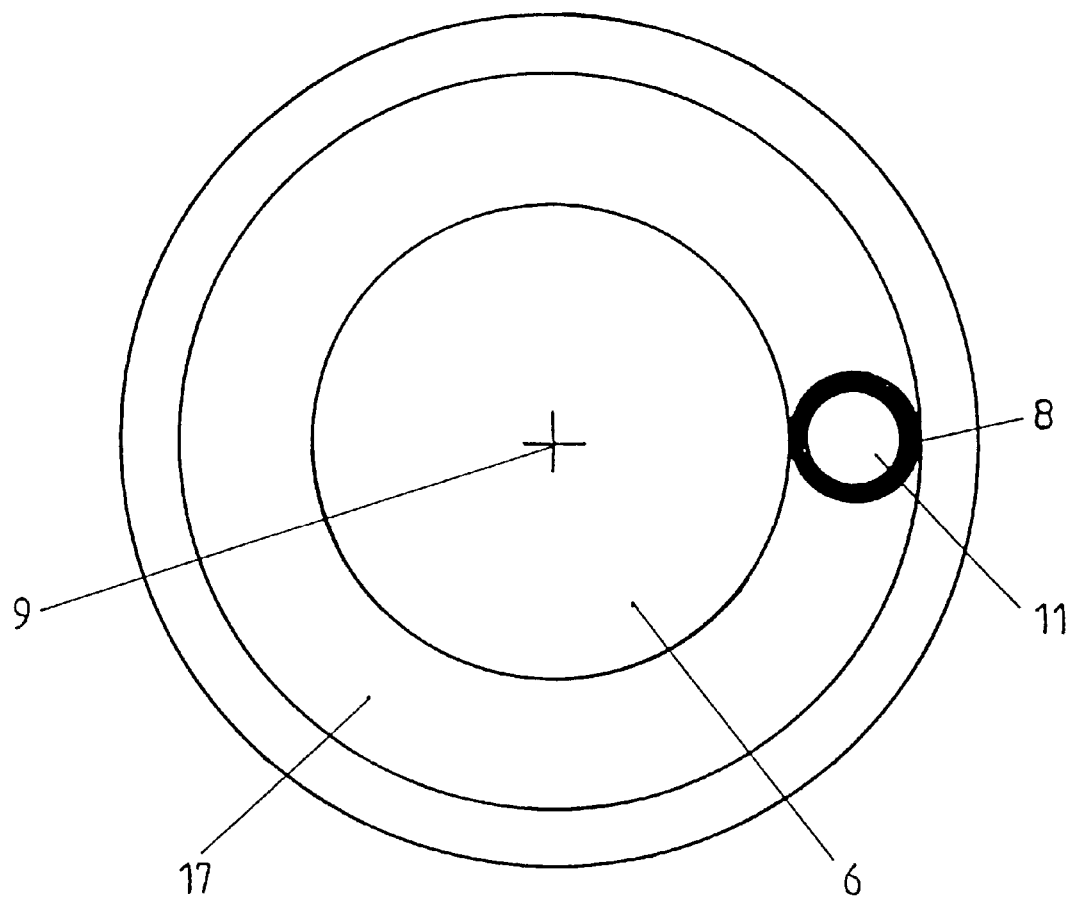
FIG. 3 is a top view of the metal plate of the test device according to FIG. 2.

The embodiment of test device 1 as depicted in FIG. 2, differs from that in FIG. 1 with respect to the metal plate 6 also forming the ignition electrode for plasma torch 4 and that no separate absorption electrode is provided. In addition, a cover 17, made of ceramic material, is provided on the metal plate 6 according to FIG. 2 where the gas jet 3 hits the bottom of the groove 10. A lining 18 of ceramic material covers the inside of the gap 11 in metal plate 6. This can also be seen from the top view according to FIG. 3, which only shows the metal plate 6. The ceramic cover 17 avoids melting of the metal plate 6 at the bottom of the groove 10 due to the impinging gas jet 3. Conduction only occurs over the regions of the metal plate 6 bordering the ceramic cover 17. The metal plate 6 carries away and distributes heat resulting from the backside of the ceramic cover 17. The ceramic lining 18 of the gap 11 protects the metal plate 6 at the gap 11 and prevents generation of conduction over the inner wall of the gap 11. The cover 17 and the lining 18 in the gap 11 jointly ensure that the flows of ions and/or electrons always have approximately the same course in the margin area of gas jet 3. The conductive parts of the metal plate 6, over which these flows pass, are always arranged with equal geometry to the gas jet 3, independent of whether or not the gap 11 lets the gas jet 3 pass.

DRAWING REFERENCE LEGEND

1—Test device
2—Sample
3—Gas jet
4—Plasma torch
5—Ignition electrode
6—Metal plate
7—Rotary drive
8—High voltage
9—Rotational axis
10—Groove 11—Gap
12—Rotary arrow
13—Controlling device
14—Valve
15—Gas feeding line
16—Absorption electrode
17—Cover
18—Lining
19—Langmuir probe

I claim:

1. A test device for impinging a sample with a high-energy gas jet, the test device comprising a plasma torch providing the gas jet heated by a plasma and directed towards the sample, wherein a massive metal plate is positioned in front of the sample, the metal plate forming the opposing electrode of the plasma torch, wherein drive means are provided for rotating the metal plate about an rotational axis, and wherein the metal plate is provided with a gap exposing the sample to the gas jet when the metal plate is in a certain rotational position about the rotational axis.

2. The test device of claim 1, wherein the drive means for rotating the metal plate about the rotational axis comprise a rotary drive which is controllable with regard to the rotational position of the metal plate about the rotational axis.

3. The test device of claim 1, wherein the gas jet hits the metal plate at the bottom of an annular groove in the surface of the metal plate.

4. The test device of claim 3, wherein the annular groove has a rounded cross section.

5. The test device of claim 3, wherein the metal plate is provided with a ceramic cover at the bottom of the groove.

6. The test device of claim 1, wherein the gap is provided with a ceramic lining.

7. The test device of claim 1, wherein the metal plate is also provided as an ignition electrode for the plasma torch.

8. The test device of claim 1, and further comprising an absorption electrode arranged in front of the sample for removing charged particles from the gas jet.

9. The test device of claim 1, and further comprising a Langmuir probe monitoring the neutrality of the gas jet in front of the sample.

* * * * *